US012788372B2

(12) United States Patent
Halmann et al.

(10) Patent No.: US 12,788,372 B2
(45) Date of Patent: Nov. 10, 2026

(54) ULTRASOUND SYSTEM WITH ADAPTIVE NON-LINEAR AXIAL SCALE

(71) Applicant: GE Precision Healthcare LLC, Waukesha, WI (US)

(72) Inventors: Menachem Halmann, Monona, WI (US); Alexander Sokulin, Kiryat Tivon (IL); Ella Sokulin, Kiryat Tivon (IL); Doron Shaked, Kiryat Tivon (IL); Or Elezra, Haifa (IL); Roei Gelbhart, Tel-Aviv (IL); Carmit Shiran, Zichron Yaakov (IL); Shreya Bhise, Milwaukee, WI (US)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 19/184,391

(22) Filed: Apr. 21, 2025

(65) Prior Publication Data

US 2026/0325107 A1 Oct. 22, 2026

(51) Int. Cl.
*A61B 8/00* (2006.01)
*G06T 3/40* (2006.01)
*G06T 7/50* (2017.01)

(52) U.S. Cl.
CPC ............ *A61B 8/5207* (2013.01); *A61B 8/465* (2013.01); *A61B 8/466* (2013.01); *G06T 3/40* (2013.01); *G06T 7/50* (2017.01); *G06T 2200/24* (2013.01); *G06T 2207/10136* (2013.01); *G06T 2207/20092* (2013.01)

(58) Field of Classification Search
CPC ........... A61B 8/5207; G06T 3/40; G06T 7/50; G06T 2207/10136
See application file for complete search history.

(56) References Cited

U.S. PATENT DOCUMENTS

| | | | | |
|---|---|---|---|---|
| 5,902,242 | A | 5/1999 | Ustuner et al. | |
| 2005/0078194 | A1 * | 4/2005 | Gonzalez | H04N 23/60 348/222.1 |
| 2015/0182999 | A1 * | 7/2015 | Zhao | G10K 11/02 310/334 |
| 2025/0045865 | A1 * | 2/2025 | Wu | G06T 3/4046 |

* cited by examiner

*Primary Examiner* — Rochelle D Turchen
(74) *Attorney, Agent, or Firm* — SPQ IP LLC

(57) ABSTRACT

An ultrasound system may acquire ultrasound data of a region of interest of a subject. The ultrasound system may generate an ultrasound image of the region of interest of the subject based on acquiring the ultrasound data of the region of interest of the subject, wherein the ultrasound image has a non-linear axial scale. The ultrasound system may display the ultrasound image having the non-linear axial scale based on generating the ultrasound image.

20 Claims, 12 Drawing Sheets

700

ULTRASOUND SYSTEM WITH ADAPTIVE NON-LINEAR AXIAL SCALE

STATEMENT REGARDING FEDERALLY SPONSORED RESEARCH AND DEVELOPMENT

This invention was made with government support under Grant No. 75A50123C00035 awarded by Biomedical Advanced Research and Development Authority (BARDA). The Government has certain rights in the invention.

TECHNICAL FIELD

The present disclosure relates to an ultrasound system that is configured to generate and display an ultrasound image having a non-linear axial scale.

BACKGROUND

Lung ultrasound is a minimally-invasive imaging modality that permits real-time visualization of pulmonary structures. Lung ultrasound permits, among other things, the assessment of pleural pathologies, such as pleurisy, pleural effusion, empyema, pleural tumors, etc. To perform lung ultrasound imaging, an ultrasound probe of an ultrasound system may transmit ultrasound signals towards a lung of a subject, and receive echo signals that are reflected by, or back-scattered from, structures of the lung of the subject. The ultrasound system may generate an ultrasound image based on the echo signals. The ultrasound image of the lung may include content, such as a pleural line, a lung line, a fractal line, A-lines, B-lines, sub-B-lines, etc. The ultrasound system may display the ultrasound image for review and assessment by a clinician. The clinician may assess any pathologies of the subject based on the various content in the ultrasound image of the lung.

An ultrasound image may have a scale that may refer to an indication of a relationship between distances on the ultrasound image and the corresponding actual distances in the subject. In general, an ultrasound image has a linear axial scale. In this case, a particular distance measured anywhere on the ultrasound image may correspond to a same actual distance in the subject. A scale may also refer to a series of visual indicators at particular intervals used to measure distances in the ultrasound image. In this case, an ultrasound image may include visual indicators that are provided at equidistant intervals.

In some cases, the content of the ultrasound image in the near-field may be relatively more clinically probative than the content of the ultrasound image in the far-field. In such cases, a clinician might be relatively more interested in viewing the content in the near-field with a greater resolution than as compared to the content in the far-field. However, the resolution of the near-field may be the same as the resolution of the far-field in an ultrasound image having a linear axial scale. As a particular example, in lung ultrasound, a clinician might be relatively more interested in visualizing pleural pathologies which generally lie at around 2 centimeters (cm) to 3 cm than as compared to visualizing B-lines which generally extend from 10 cm through 18 cm. Notwithstanding, the clinician might still be interested in visualizing both the pleura and the B-lines in order to perform an assessment. These two interests might be contradictory in some scenarios, particularly with sector two-dimensional (2D) or three-dimensional (3D) probes, due to their narrow field of view at shallow depths. This results in sub-optimal pleura visualization when the image depth is set for optimal B-line visualization.

SUMMARY

This summary introduces concepts that are described in more detail in the detailed description. It should not be used to identify essential features of the claimed subject matter, nor to limit the scope of the claimed subject matter.

In an aspect, an ultrasound system may include a lens, an acoustic matching layer, an acoustic dematching layer, and a plurality of transducer elements; a memory configured to store instructions; and one or more processors configured to execute the instructions to: acquire ultrasound data of a region of interest of a subject; generate an ultrasound image of the region of interest of the subject based on acquiring the ultrasound data of the region of interest of the subject, wherein the ultrasound image has a non-linear axial scale; and display the ultrasound image having the non-linear axial scale based on generating the ultrasound image.

In an aspect, the one or more processors may be further configured to transform, before performing scan conversion, raw ultrasound data such that a first region of the ultrasound image has a first linear axial scale and a second region of the ultrasound image has a second linear axial scale that is different than the first linear axial scale.

In an aspect, the one or more processors may be further configured to transform, before performing scan conversion, raw ultrasound data by applying u-law scaling.

In an aspect, the one or more processors may be further configured to determine a depth at which to transition a scale of the ultrasound image.

In an aspect, a first region of the ultrasound image includes a first linear axial scale, and wherein a second region of the ultrasound image includes a second linear axial scale that is different than the first linear axial scale.

In an aspect, the ultrasound image includes a first region corresponding to a first range of depths in the subject, wherein the ultrasound image includes a second region corresponding to a second range of depths in the subject, wherein the first range of depths is the same as the second range of depths, and wherein the first region includes a first number of pixels that is greater than a second number of pixels in the second region.

In an aspect, the ultrasound image is a single continuous ultrasound image.

In another aspect, a method may include acquiring ultrasound data of a region of interest of a subject; generating an ultrasound image of the region of interest of the subject based on acquiring the ultrasound data of the region of interest of the subject, wherein the ultrasound image has a non-linear axial scale; and displaying the ultrasound image having the non-linear axial scale based on generating the ultrasound image.

In an aspect, the method may include transforming, before performing scan conversion, raw ultrasound data such that a first region of the ultrasound image has a first linear axial scale and a second region of the ultrasound image has a second linear axial scale that is different than the first linear axial scale.

In an aspect, the method may include transforming, before performing scan conversion, raw ultrasound data by applying u-law scaling.

In an aspect, the method may include determining a depth at which to transition a scale of the ultrasound image.

In an aspect, a first region of the ultrasound image includes a first linear axial scale, and a second region of the ultrasound image includes a second linear axial scale that is different than the first linear axial scale.

In an aspect, the ultrasound image includes a first region corresponding to a first range of depths in the subject, wherein the ultrasound image includes a second region corresponding to a second range of depths in the subject, wherein the first range of depths is the same as the second range of depths, and wherein the first region includes a first number of pixels that is greater than a second number of pixels in the second region.

In an aspect, the ultrasound image is a single continuous ultrasound image.

In yet another aspect, a non-transitory computer-readable medium storing instructions that, when executed by one or more processors, cause the one or more processors to: acquire ultrasound data of a region of interest of a subject; generate an ultrasound image of the region of interest of the subject based on acquiring the ultrasound data of the region of interest of the subject, wherein the ultrasound image has a non-linear axial scale; and display the ultrasound image having the non-linear axial scale based on generating the ultrasound image.

In an aspect, the instructions may further cause the one or more processors to transform, before performing scan conversion, raw ultrasound data such that a first region of the ultrasound image has a first linear axial scale and a second region of the ultrasound image has a second linear axial scale that is different than the first linear axial scale.

In an aspect, the instructions may further cause the one or more processors to transform, before performing scan conversion, raw ultrasound data by applying u-law scaling.

In an aspect, the instructions may further cause the one or more processors to determine a depth at which to transition a scale of the ultrasound image.

In an aspect, a first region of the ultrasound image includes a first linear axial scale, and a second region of the ultrasound image includes a second linear axial scale that is different than the first linear axial scale.

In an aspect, the ultrasound image includes a first region corresponding to a first range of depths in the subject, wherein the ultrasound image includes a second region corresponding to a second range of depths in the subject, wherein the first range of depths is the same as the second range of depths, and wherein the first region includes a first number of pixels that is greater than a second number of pixels in the second region.

DETAILED DESCRIPTION

As addressed above, in some cases, content of an ultrasound image in the near-field may be relatively more clinically probative than the content of the ultrasound image in the far-field. In such cases, a clinician may be relatively more interested in viewing the content in the near-field with a greater resolution than as compared to the content in the far-field. However, the resolution of the near-field may be the same as the resolution of the far-field in an ultrasound image having a linear axial scale.

Some embodiments herein provide an ultrasound system that may acquire ultrasound data of a region of interest of a subject; generate an ultrasound image of the region of interest of the subject, the ultrasound image having a non-linear axial scale based on acquiring the ultrasound data of the region of interest of the subject; and display the ultrasound image having the non-linear axial scale based on generating the ultrasound image. For example, in the context of lung ultrasound, the ultrasound system may transform raw ultrasound data along the axial axis based on the pleura location, so that the pleura is presented with high resolution while B-lines extend as straight lines in lower resolution until the end of the ultrasound image. In this way, the embodiments herein permit a clinician to observe the near-field details while appreciating the full imaging depth in a single continuous ultrasound image.

Accordingly, some embodiments herein provide an improvement to the technical field of ultrasound imaging by providing for the generation of a new type of ultrasound image that is a single continuous image that has a non-linear axial scale. Further, some embodiments herein provide an improvement to ultrasound systems by permitting the ultrasound system to generate a single continuous image that has a non-linear axial scale. The non-linear axial scale may permit the simultaneous viewing of the near-field and the far-field in a manner that provides for increased detail and resolution in the near-field. Accordingly, a clinician may observe the near-field details while appreciating the full imaging depth in a single continuous ultrasound image.

Figure 1:
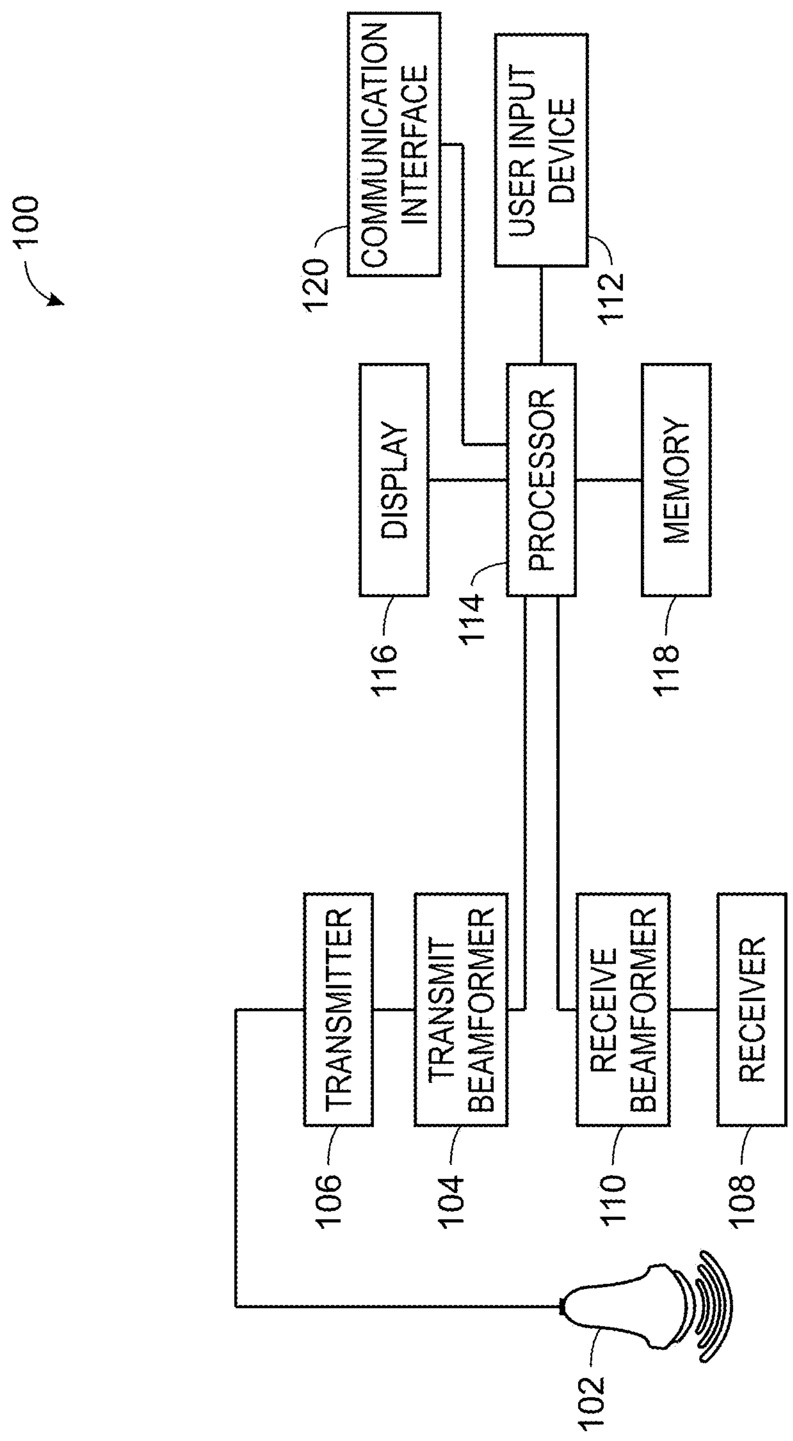
FIG. 1 is a diagram of example components of an ultrasound system for generating and displaying an ultrasound image having a non-linear axial scale.

FIG. 1 is a diagram of example components of an ultrasound system 100 for generating and displaying an ultrasound image having a non-linear axial scale. As shown in FIG. 1, the ultrasound system 100 may include an ultrasound probe 102, a transmit beamformer 104, a transmitter 106, a receiver 108, a receive beamformer 110, a user input device 112, a processor 114, a display 116, a memory 118, and a communication interface 120. The foregoing components may be connected via wired or wireless connections.

The ultrasound probe 102 may be configured to acquire ultrasound data. For example, the ultrasound probe 102 may be a linear probe, a phase array probe, a curved linear probe coupled with a position tracking system, a mechanically steered linear array transducer, a phased array transducer, a curved linear array transducer, an electronically steered 2D transducer array, an electronic 3D (e3D) probe, an electronic 4d (e4D) probe, a low profile wearable patch version of any of the foregoing probes, or the like. According to an embodiment, the ultrasound probe 102 may be configured to generate ultrasound signals, emit the ultrasound signals towards the region of interest of a subject, receive echo ultrasound signals that are back-scattered from the region of interest of the subject, generate ultrasound data based on the echo ultrasound signals, and output the ultrasound data.

The transmit beamformer 104 may be configured to apply delay times to electrical signals provided to elements of the ultrasound probe 102 to focus corresponding ultrasound signals at the region of interest. The transmitter 106 may be configured to transmit electrical signals to the elements of the ultrasound probe 102 to drive the elements of the ultrasound probe 102 to emit ultrasound signals towards the region of interest. The elements of the ultrasound probe 102 may be configured to receive the electrical signals from the transmitter 106, convert the electrical signals into ultrasound signals, and emit the ultrasound signals towards the region of interest. The elements of the ultrasound probe 102 may be configured to receive echo ultrasound signals that are back-scattered by the region of interest, convert the echo ultrasound signals into electrical signals, and provide the electrical signals to the receiver 108. The receiver 108 may be configured to receive electrical signals from the elements, and provide the electrical signals to the receive beamformer 110. The receive beamformer 110 may apply delay times to the electrical signals received from the elements of the ultrasound probe 102.

The user input device 112 may be configured to receive a user input, and provide the user input to the processor 114. The user input device 112 may be a user interface. For example, the user input device 112 may be a touch screen display, a keyboard, a keypad, a mouse, a button, a switch, a microphone, or the like. Additionally, or alternatively, the user input device 112 may be configured to sense information. For example, the user input device 112 may sense information from an electro-magnetic positioning system, an inertial measurement system, an accelerometer, a gyroscope, an actuator, or the like.

The processor 114 may be configured to perform the operations as described herein. For example, the processor 114 may be a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. The processor 114 may be implemented in hardware, firmware, or a combination of hardware and software. The processor 114 may include one or more processors 114 configured to perform the operations described herein. For example, a single processor 114 may be configured to perform all of the operations described herein. Alternatively, multiple processors 114, collectively, may be configured to perform all of the operations described herein, and each of the multiple processors 114 may be configured to perform a subset of the operations described herein. For example, a first processor 114 may perform a first subset of the operations described herein, a second processor 114 may be configured to perform a second subset of the operations described herein, etc.

The processor 114 may be configured to control the ultrasound probe 102 to acquire ultrasound data. The processor 114 may be configured to control which of the elements of the ultrasound probe 102 are active, and control the shape of a beam emitted from the ultrasound probe 102. The processor 114 may generate ultrasound images for display. For example, the processor 114 may generate B-mode images, color Doppler images, M-mode images, color M-mode images, or the like. The ultrasound images may be 3D images, 2D images, single plane images, bi-plane images, three-plane images, multi-plane images, or the like. The ultrasound images may correspond to various anatomical planes (e.g., sagittal, coronal, and transverse) of the region of interest.

The processor 114 may perform scan conversion. For example, the processor 114 may perform scan conversion by converting raw ultrasound data in a scan format to a display format. Restated, the processor 114 may convert the raw ultrasound data from a Polar coordinate format to ultrasound data for display in a Cartesian coordinate format.

The display 116 may be configured to display information. For example, the display 116 may be a monitor, an LED display, a cathode ray tube, a projector display, a touchscreen, tablet computer, mobile phone, or the like. The display 116 may display ultrasound images based on the ultrasound data in real-time. For example, the display 116 may display the ultrasound images within one second, two seconds, five seconds, etc., of the ultrasound data being acquired by the ultrasound probe 102.

The memory 118 may be configured to store information and/or instructions for use by the processor 114. The memory 118 may be a non-transitory computer-readable medium. For example, the memory 118 may be a random access memory (RAM), a read only memory (ROM), and/or another type of dynamic or static storage device (e.g., a flash memory, a magnetic memory, and/or an optical memory) that stores information and/or instructions for use by the processor 114. The memory 118 may be configured to store instructions that, when executed by the processor 114, cause the processor 114 to perform the operations described herein.

The communication interface 120 may be configured to enable the processor 114 to communicate with other systems, such as via a wired connection, a wireless connection, or a combination of wired and wireless connections. For example, the communication interface 120 may include an Ethernet interface, an optical interface, a coaxial interface, an infrared interface, a radio frequency (RF) interface, a universal serial bus (USB) interface, a Wi-Fi interface, a cellular network interface, or the like.

The number and arrangement of the components of the ultrasound system 100 shown in FIG. 1 are provided as an example. In practice, the ultrasound system 100 may include additional components, fewer components, different components, or differently arranged components than those shown in FIG. 1. Additionally, or alternatively, a set of components (e.g., one or more components) of the ultrasound system 100 may perform one or more functions described as being performed by another set of components of the ultrasound system 100.

Figure 2:
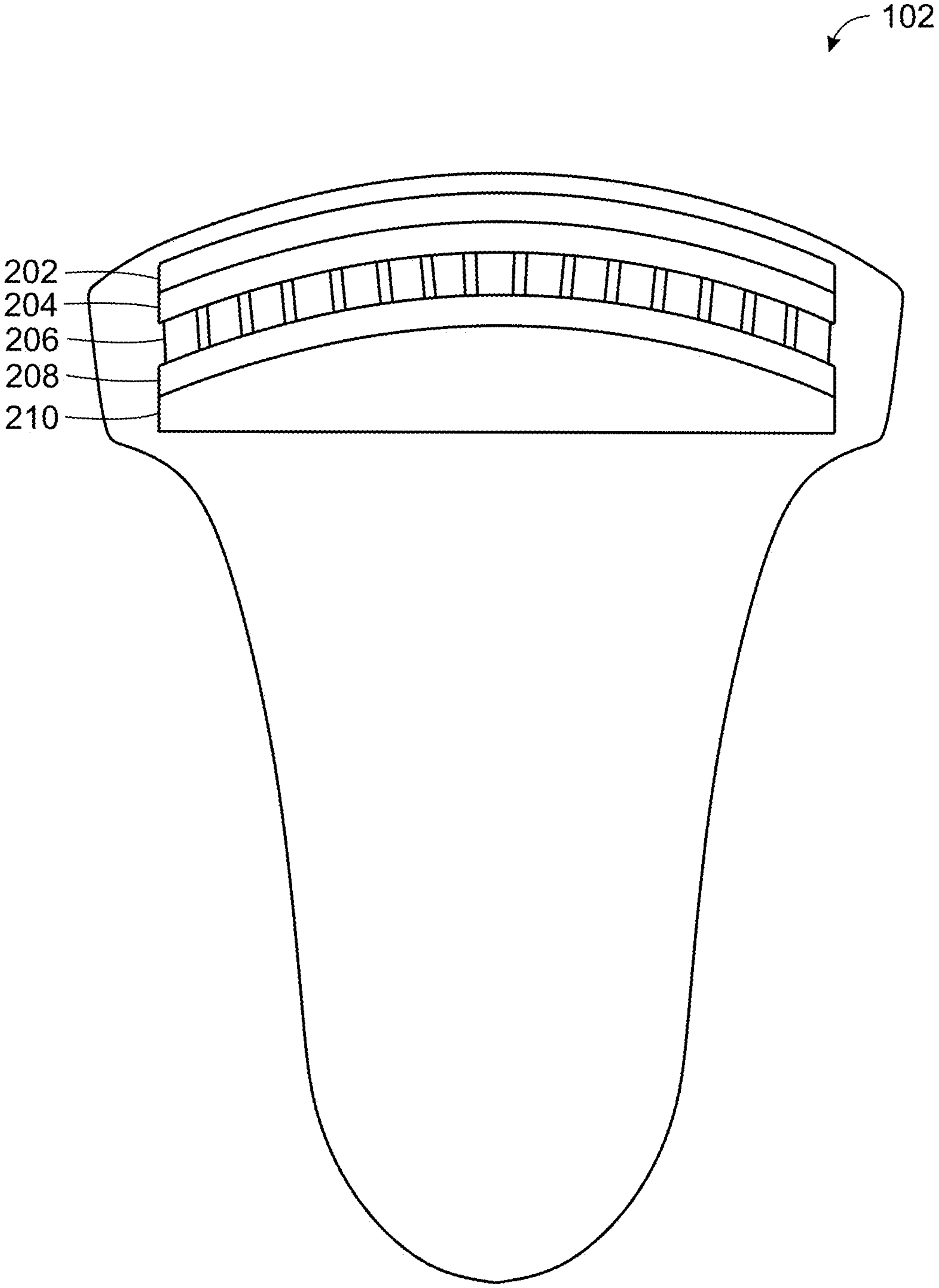
FIG. 2 is a diagram of an example ultrasound probe of the ultrasound system for generating and displaying an ultrasound image having a non-linear axial scale.

FIG. 2 is a diagram of an example ultrasound probe 102 of the ultrasound system 100 for generating and displaying an ultrasound image having a non-linear axial scale. As shown in FIG. 2, the ultrasound probe 102 may include a lens 202, an acoustic matching layer 204, transducer elements 206, an acoustic dematching layer 208, and a backing layer 210.

According to an embodiment, the lens 202 may be configured to direct an ultrasound signal towards the region of interest of the subject. For example, the lens 202 may be silicone, epoxy, rubber, or the like. According to an embodiment, the acoustic matching layer 204 may be configured to facilitate matching of an impedance differential that may exist between the relatively high impedance transducer elements 206 and the relatively low impedance subject. For example, the acoustic matching layer 204 may be graphite, plastic, resin, or the like. According to an embodiment, the transducer elements 206, respectively, may be configured to receive an element specific transmit signal, deform based on the element specific transmit signal, generate an ultrasound signal based on the deformation, and transmit the ultrasound signal towards a region of interest. Additionally, or alternatively, the transducer elements 206 may be configured to receive an echo signal reflected by or backscattered from the region of interest, deform based on the echo signal, generate an electrical signal based on the deformation, and transmit the electrical signal. For example, the transducer elements 206 may be piezoelectric materials, such as $Pb(Mg_{1/3}Nb_{2/3})O_3$—$PbTiO_3$ ("PMN-PT"), $Pb(In_{1/2}Nb_{1/2})O_3$—$Pb(Mg_{1/3}Nb_{2/3})O_3$—$PbTiO_3$ ("PIN-PMN-PT"), Pb(ZrTi) ("PZT"), or the like. According to an embodiment, the acoustic dematching layer 208 may be configured to decrease insertion losses and enhance a frequency bandwidth of the transducer elements 206. For example, the acoustic dematching layer 208 may be tungsten carbide, silicon carbide, or the like. According to an embodiment, the backing layer 210 may be configured to attenuate ultrasound signals directed from the transducer elements 206 in a direction opposite to the subject, and attenuate ultrasound signals deflected by a housing of the ultrasound probe 102. For example, the backing layer 210 may be an epoxy, a metal, or the like.

The number and arrangement of the components of the ultrasound probe 102 shown in FIG. 2 are provided as an example. In practice, the ultrasound probe 102 may include additional components, fewer components, different components, or differently arranged components than those shown in FIG. 2. Additionally, or alternatively, a set of components (e.g., one or more components) of the ultrasound probe 102 may perform one or more functions described as being performed by another set of components of the ultrasound probe 102.

Figure 3:
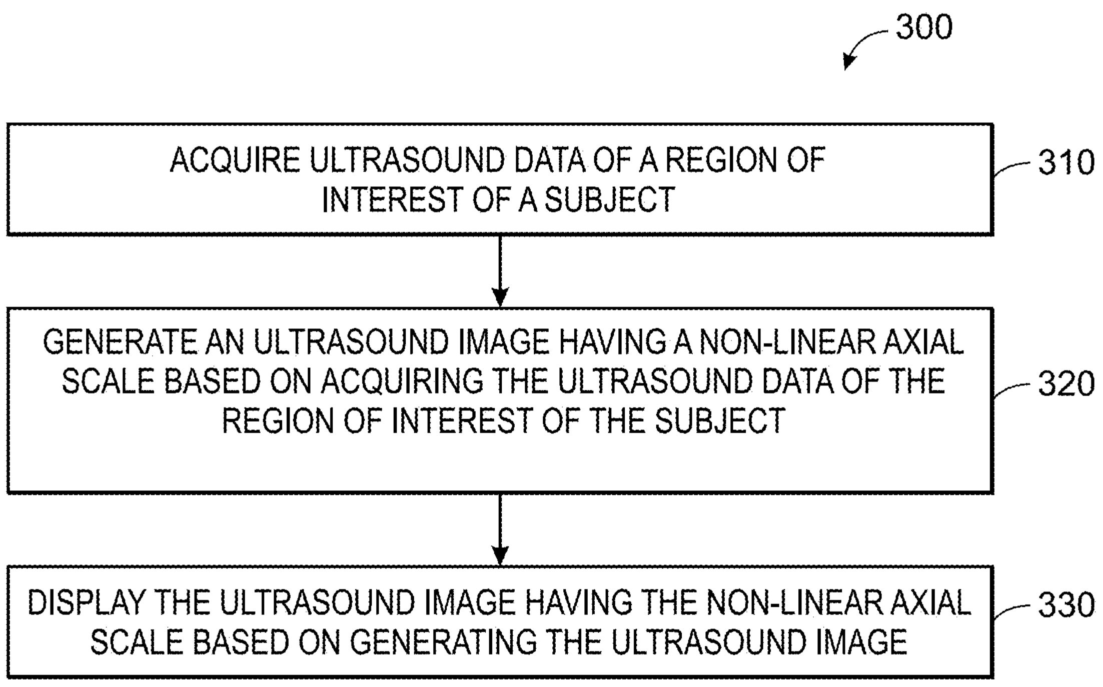
FIG. 3 is a flowchart of an example process for generating and displaying an ultrasound image having a non-linear axial scale.

FIG. 3 is a flowchart of an example process 300 for generating and displaying an ultrasound image having a non-linear axial scale. As shown in FIG. 3, the process 300 may include acquiring ultrasound data of a region of interest of a subject (operation 310). For example, the ultrasound system 100 may acquire ultrasound data of a region of interest of a subject. The ultrasound system 100 may control the ultrasound probe 102 to transmit ultrasound signals towards a region of interest of a subject, and control the ultrasound probe 102 to receive echo signals reflected by, or back-scattered from, the region of interest of the subject. The subject may be a human, an animal, a phantom, an object, or the like. The region of interest may be any region of the subject. For example, the region of interest may be a lung, a heart, a liver, or the like. In the context of lung ultrasound, the region of interest may depict pleura.

As further shown in FIG. 3, the process 300 may include generating an ultrasound image having a non-linear axial scale based on acquiring the ultrasound data of the region of interest of the subject (operation 320). For example, the ultrasound system 100 may generate an ultrasound image having a non-linear axial scale based on acquiring the ultrasound data of the region of interest of the subject.

As used herein, a "scale" may refer to an indication of a relationship between a distance on an ultrasound image and a corresponding actual distance in the subject. In this case, and as used herein, a "linear axial scale" may refer to a scale in which a particular axial distance on the ultrasound image, measured at any point of the ultrasound image, corresponds to a same actual axial distance in the subject. As an example, assume a user interface element (e.g., a line) has a fixed length (e.g., 2 cm). If the user interface element is positioned at any point on the ultrasound image, the actual axial distance (e.g., 3 cm) in the subject is the same. For example, if the line is positioned at a first position, the actual axial distance in the subject is 3 cm. If the line is positioned at a second position (or any other position) in the ultrasound image, the actual axial distance in the subject is 3 cm.

Further, and as used herein, a "non-linear axial scale" may refer to a scale in which a particular axial distance on the ultrasound image, measured at various points on the ultrasound image, may correspond to a different actual axial distance in the subject. As an example, assume a user interface element (e.g., a line) has a fixed length (e.g., 2 cm). The actual axial distance in the subject depends on where the line is positioned. For example, if the line is positioned at a first position, the actual axial distance in the subject is 3 cm. If the line is positioned at a second position in the ultrasound image, the actual axial distance in the subject may be 5 cm.

As used herein, a "scale" may also refer to a series of visual indictors (e.g., marks, dots, lines, points, etc.) at particular intervals that are used to measure distances in the subject. In this case, and as used herein, "linear axial scale" may refer to a series of visual indicators that are provided at a same non-changing interval. Restated, the respective distances between any two visual indicators are the same. Further, and as used herein, "non-linear axial scale" may refer to a series of visual indicators that are provided at a changing interval. Restated, the respective distances between any two visual indicators may, or might not, be the same.

According to an embodiment, the ultrasound system 100 may generate the ultrasound image having a non-linear axial scale by transforming raw ultrasound data such that a resolution of a first region of the ultrasound image is greater than a second region of the ultrasound image. A resolution may refer to a number of pixels in the ultrasound image or a number of pixels on the display 116 of the ultrasound system 100. The raw ultrasound data may refer to ultrasound data acquired via the ultrasound probe 102, and that has not yet been processed via a scan conversion process. The resolution of a first region may be greater than a resolution of a second region according to the non-linear axial scale. For example, the first region may have a first number of pixels that is greater than a second number of pixels of the second region. The first region may correspond to a first range of depths (e.g., 0-2 cm, 0-3 cm, 1-2 cm, or the like), and the second region may correspond to a second range of depths (e.g., 2-4 cm, 4-6 cm, 7-8 cm, 10-14 cm, or the like).

According to an embodiment, the ultrasound system 100 may transform the raw ultrasound data such that a first region of the ultrasound image has a first linear axial scale and a second region of the ultrasound image has a second linear axial scale that is different than the first linear axial scale. In this way, the ultrasound image may have a non-linear axial scale because the ultrasound image has, at least, two different linear axial scales. The ultrasound image may have any number of different linear axial scales. For example, the ultrasound image may have n different regions having n different linear axial scales. According to another embodiment, the ultrasound system 100 may transform the raw ultrasound data by applying u-law scaling. The ultrasound system 100 may use different compression values (e.g., k-values). The ultrasound system 100 may apply u-law scaling through the entire ultrasound image. Alternatively, the ultrasound system 100 may apply u-law scaling at a particular depth of the ultrasound image. It should be understood that the ultrasound system 100 may use any other type of technique to apply a non-linear axial scale to the ultrasound image.

In the context of lung ultrasound, and by transforming the raw ultrasound data before performing scan conversion, the ultrasound system 100 may maintain the appearance of B-lines as compared to if the non-linear axial scale was applied to ultrasound data that had already been scan converted. For instance, B-lines are acoustic artifacts that follow the direction of the ultrasound transmission beam in the axial direction. By transforming the raw ultrasound data, the ultrasound system 100 may maintain straight B-lines. In contrast, if the ultrasound system 100 transformed the scan converted ultrasound data, the non-linearity in Cartesian direction would result in the appearance of curved B-lines.

According to an embodiment, the ultrasound image may be a single continuous ultrasound image that exhibits the non-linear axial scale. That is, the ultrasound image might not include a zoomed-in portion, a zoomed-out portion, a discontinuous portion, or the like.

As further shown in FIG. 3, the process 300 may include displaying the ultrasound image having the non-linear axial scale based on generating the ultrasound image (operation 330). For example, the ultrasound system 100 may display the ultrasound image having the non-linear axial scale based on generating the ultrasound image. In this way, the ultrasound image may display a first region having a higher resolution and a second region having a lower resolution, which may permit a clinician to assess the first region in greater detail while still being able to visualize the second region. As an example, in the context of lung ultrasound, the clinician may visualize the pleura in more detail while still being able to visualize the B-lines.

Figure 4A:
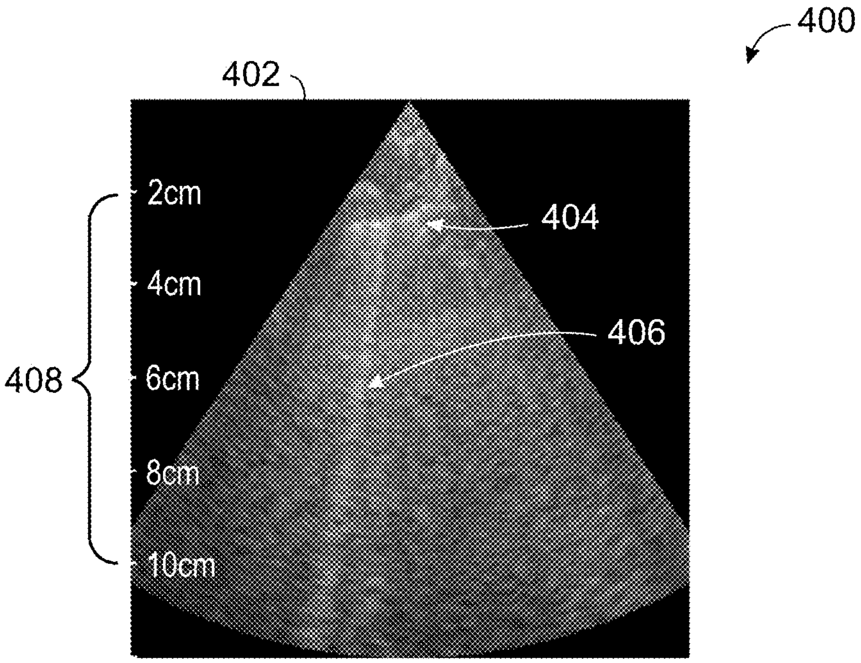
FIG. 4A is a diagram of an example ultrasound image having a linear axial scale.

FIG. 4A is a diagram 400 of an example ultrasound image 402 having a linear axial scale. As shown in FIG. 4A, the ultrasound image 402 may display a pleural line 404 and a B-line 406. The ultrasound image 402 has a linear axial scale in that a particular axial distance on the ultrasound image 402, measured at any point of the ultrasound image 402, corresponds to a same actual axial distance in the subject. Further, the ultrasound image 402 has a linear axial scale in that a series of visual indicators 408 are provided at a same non-changing interval. Restated, the distance between the visual indicator of "2 cm" and "4 cm" is the same as the distance between the visual indicator of "4 cm" and "6 cm," etc.

Figure 4B:
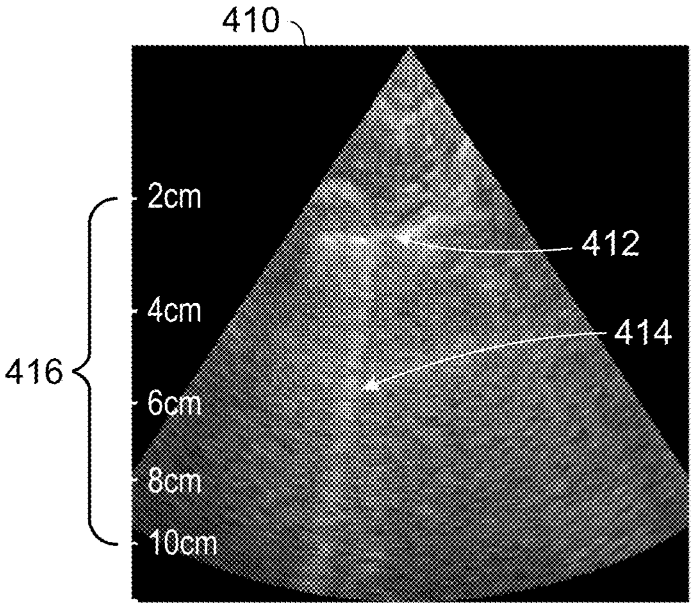
FIG. 4B is a diagram of an example ultrasound image having a non-linear axial scale.

FIG. 4B is a diagram 400 of an example ultrasound image 410 having a non-linear axial scale. As shown in FIG. 4B, the ultrasound image 410 may display a pleural line 412 and a B-line 414. The ultrasound image 410 has a non-linear axial scale in that a particular axial distance on the ultrasound image 410, measured at any point of the ultrasound image 410, may correspond to a same actual axial distance in the subject or a different axial distance in the subject. Further, the ultrasound image 410 has a non-linear axial scale in that a series of visual indicators 416 are provided at a changing interval. Restated, the distance between the visual indicator of "2 cm" and "4 cm" is the same as the distance between the visual indicator of "4 cm" and "6 cm," however the distance between the visual indicator of "8 cm" and "10 cm" is different than, for instance, the distance between the visual indicator of "2 cm" and "4 cm."

In this way, the resolution of the region between 0 cm through 4 cm in the ultrasound image 410 may be greater than the resolution of the region between 0 cm through 4 cm in the ultrasound image 402. Accordingly, a clinician may more readily assess the pleural line 412. Further, the resolution of the region between 6 cm through 10 cm in the ultrasound image 410 may be lower than the resolution of the region between 6 cm through 10 cm in the ultrasound image 402. However, the clinician may still nonetheless be capable of visualizing the B-line 414 in the ultrasound image 410.

Figure 5:
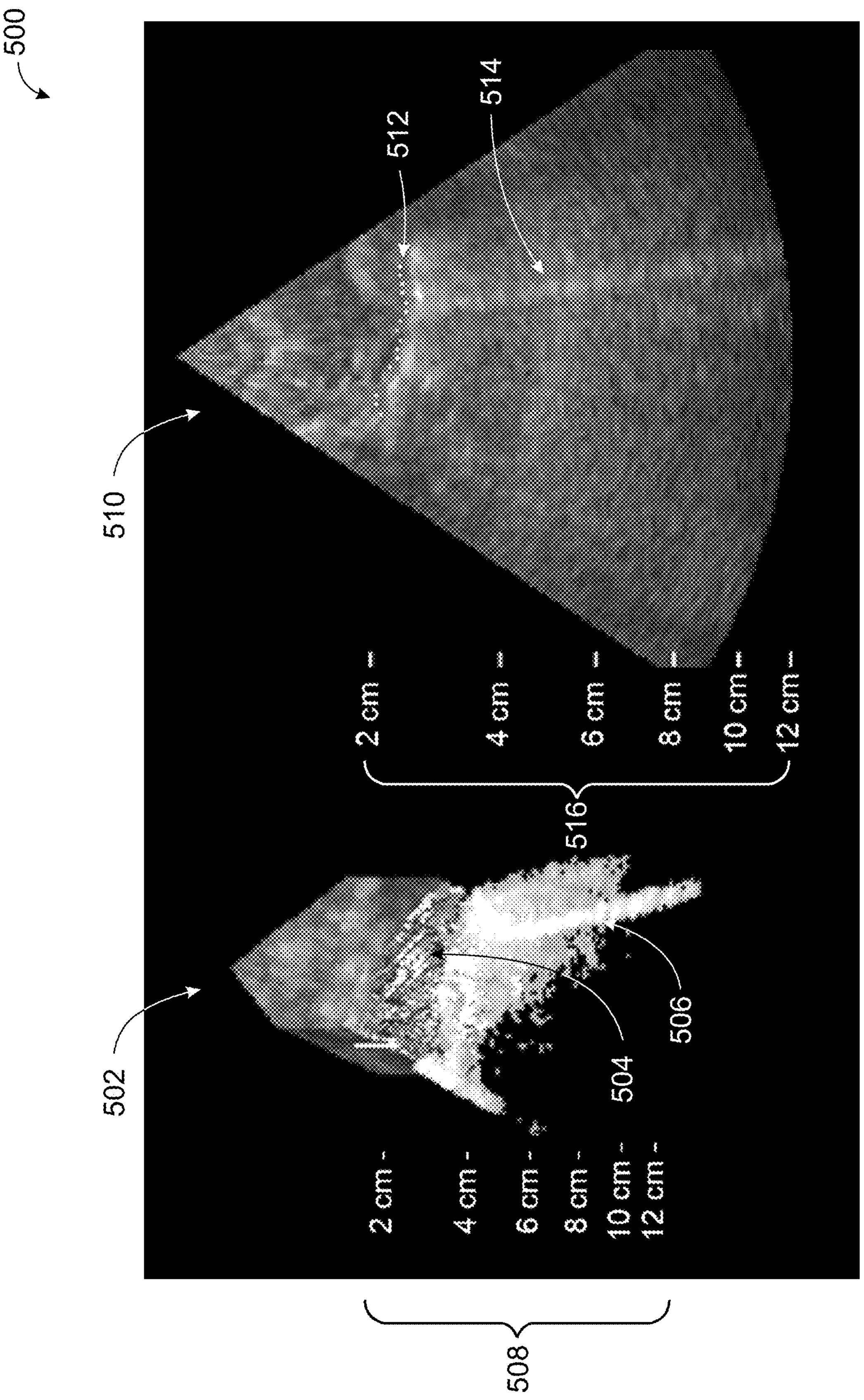
FIG. 5 is a diagram of an example 3D ultrasound image having a non-linear axial scale.

FIG. 5 is a diagram 500 of an example three-dimensional (3D) ultrasound image 502 having a non-linear axial scale. As shown in FIG. 5, the 3D ultrasound image 502 may display a pleural line 504 and a B-line 506. The 3D ultrasound image 502 has a non-linear axial scale in that a particular axial distance on the 3D ultrasound image 502, measured at any point of the 3D ultrasound image 502, may correspond to a same actual axial distance in the subject or a different axial distance in the subject. Further, the 3D ultrasound image 502 has a non-linear axial scale in that a series of visual indicators 508 are provided at a changing interval. Restated, the distance between the visual indicator of "2 cm" and "4 cm" is the same as the distance between the visual indicator of "4 cm" and "6 cm," however the distance between the visual indicator of "8 cm" and "10 cm" is different than, for instance, the distance between the visual indicator of "2 cm" and "4 cm." As further shown in FIG. 5, the ultrasound system 100 may also display a 2D ultrasound image 510 corresponding to a particular slice of the 3D ultrasound image 502. The 2D ultrasound image 510 may display a pleural line 512 and a B-line 514. The 2D ultrasound image 510 has a non-linear axial scale in that a particular axial distance on the 2D ultrasound image 510, measured at any point of the 2D ultrasound image 510, may correspond to a same actual axial distance in the subject or a different axial distance in the subject. Further, the 2D ultrasound image 510 has a non-linear axial scale in that a series of visual indicators 516 are provided at a changing interval. Restated, the distance between the visual indicator of "2 cm" and "4 cm" is the same as the distance between the visual indicator of "4 cm" and "6 cm," however the distance between the visual indicator of "8 cm" and "10 cm" is different than, for instance, the distance between the visual indicator of "2 cm" and "4 cm."

Figure 6:
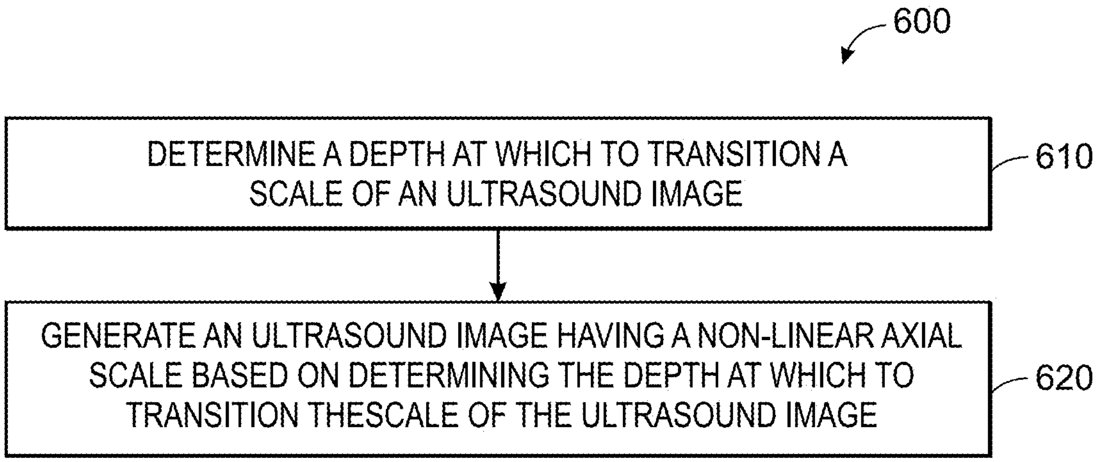
FIG. 6 is a flowchart of an example process for determining a depth at which to transition a scale of an ultrasound image.

FIG. 6 is a flowchart of an example process 600 for determining a depth at which to transition a scale of an ultrasound image. As shown in FIG. 6, the process 600 may include determining a depth at which to transition a scale of an ultrasound image (operation 610). For example, the ultrasound system 100 may determine a depth at which to transition a scale of an ultrasound image.

According to an embodiment, the ultrasound system 100 may determine the depth at which to transition a scale of an ultrasound image using an image processing technique. For example, the image processing technique may be a segmentation technique, a pattern matching technique, a feature extraction technique, an image analysis technique, an edge detection technique, an image registration technique, or the like. In this case, the ultrasound system 100 may analyze the ultrasound image using the image processing technique, and determine the depth at which to transition the scale based on the analysis. For example, the ultrasound system 100 may analyze the ultrasound image to identify one or more structures that can be used to demarcate where to transition the scale. In the context of lung ultrasound, the one or more structures may be pleura.

According to another embodiment, the ultrasound system 100 may determine the depth at which to transition a scale of an ultrasound image using an AI model. For example, the ultrasound system 100 may input an ultrasound image into the AI model, and determine the depth at which to transition a scale of an ultrasound image based on an output of the AI model. The AI model may be a convolutional neural network (CNN) model, a residual neural network, a random forest model, a decision tree model, an artificial neural network (ANN), a Naïve Bayes model, a decision tree, a recurrent neural network (RNN), a logistic regression model, a support vector machine, or the like. In this case, the AI model may be trained to receive an ultrasound image, analyze the ultrasound image to determine the depth at which to transition a scale of an ultrasound image, and output information that identifies the depth at which to transition a scale of an ultrasound image. The training data may include known ultrasound images that are correlated with known depths at which to transition scales of ultrasound images.

According to an embodiment, the ultrasound system 100 may determine the depth at which to transition a scale of an ultrasound image using predetermined information corresponding to the subject. For example, the predetermined information may identify the depth, and may be correlated with a gender of the subject, a physical characteristic (e.g., height, weight, body mass index, etc.) of the subject, an age of the subject, or the like. In the context of lung ultrasound, the depth may correspond to a depth of the pleura, and may be an average depth of the pleura for a population, or the like.

According to an embodiment, the ultrasound system 100 may determine the depth at which to transition a scale of an ultrasound image based on a particular region of interest being scanned. For example, the ultrasound system 100 may determine the particular region of interest based on analyzing the ultrasound image, based on tracking data of the ultrasound probe 102, based on position data of the subject, or the like. In the context of lung ultrasound, the depth may be shallower for upper zones of the lung, and may be deeper for lower zones of the lung.

According to an embodiment, the ultrasound system 100 may determine the depth at which to transition a scale of an ultrasound image using preoperative imaging data of the region of interest acquired by a preoperative imaging system (e.g., a computed tomography (CT) system, a magnetic resonance imaging (MRI) system, an ultrasound system, an X-ray system, a positron emission tomography (PET) device, or the like). For example, the ultrasound system 100 may register the ultrasound image with a preoperative image, and determine the depth at which to transition a scale of an ultrasound image based on registering the ultrasound image with a preoperative image. In this case, the preoperative imaging data may identify the depth at which to transition a scale of an ultrasound image.

According to an embodiment, the ultrasound system 100 may determine the depth at which to transition a scale of an ultrasound image based on a user input received via the user input device 112. For example, a user of the ultrasound system 100 may interact with the user input device 112 to select the depth at which to transition a scale of an ultrasound image. The ultrasound system 100 may determine the depth at which to transition a scale of an ultrasound image based on the selection.

As further shown in FIG. 6, the process 600 may include generating an ultrasound image having a non-linear axial scale based on determining the depth at which to transition the scale of the ultrasound image (operation 620). For example, the ultrasound system 100 may generate an ultrasound image having a non-linear axial scale based on acquiring the ultrasound data of the region of interest of the subject in a similar manner as described above in connection with operation 320 of FIG. 3. The ultrasound system 100 may use the determined depth to transform the raw ultrasound data such that the ultrasound image includes a non-linear axial scale. For example, the ultrasound system 100 may transform the raw ultrasound data at depths that are shallower than the determined depth such to have a greater resolution than as compared to the raw ultrasound data at depths that are deeper than the determined depth.

Figure 7A:
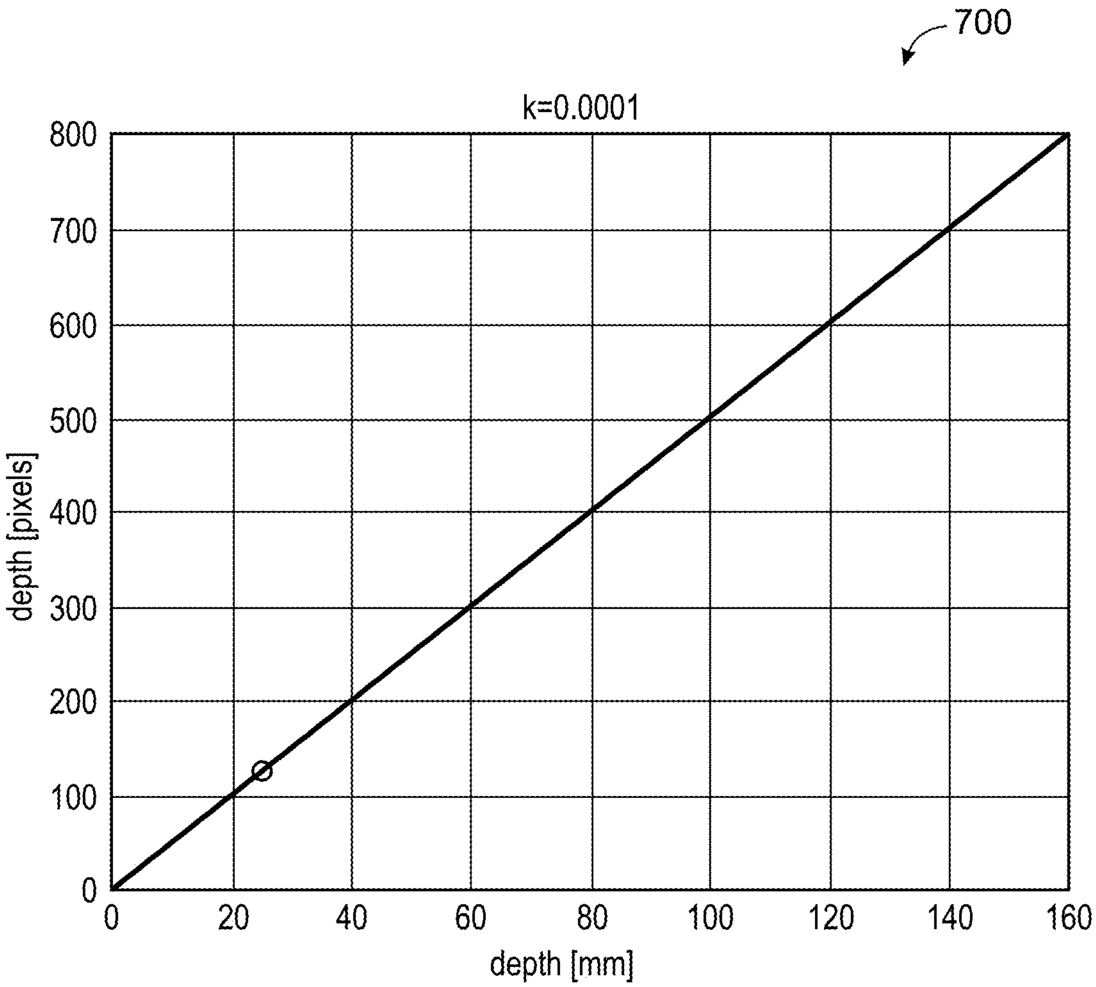
FIGS. 7A-7C are diagrams of scaling techniques for generating an ultrasound image having a non-linear axial scale.
Figure 7B:
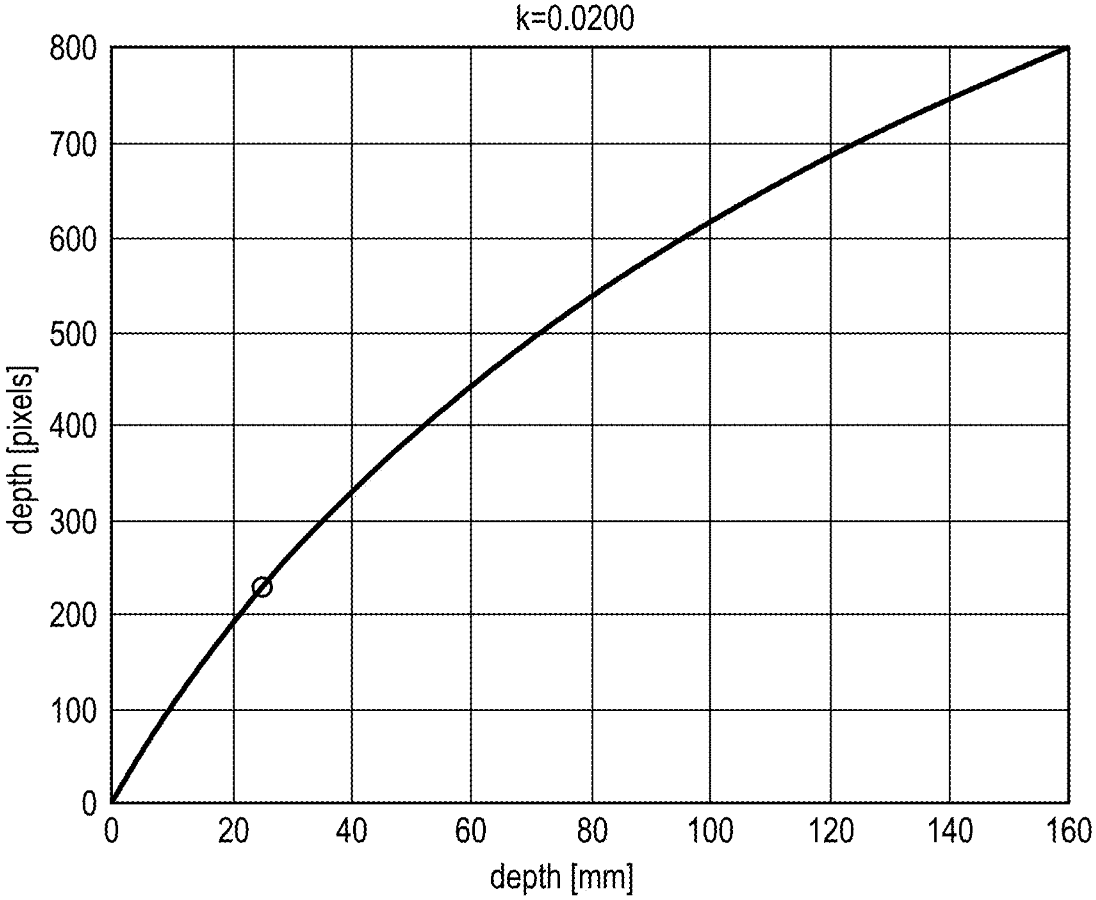
Figure 7C:
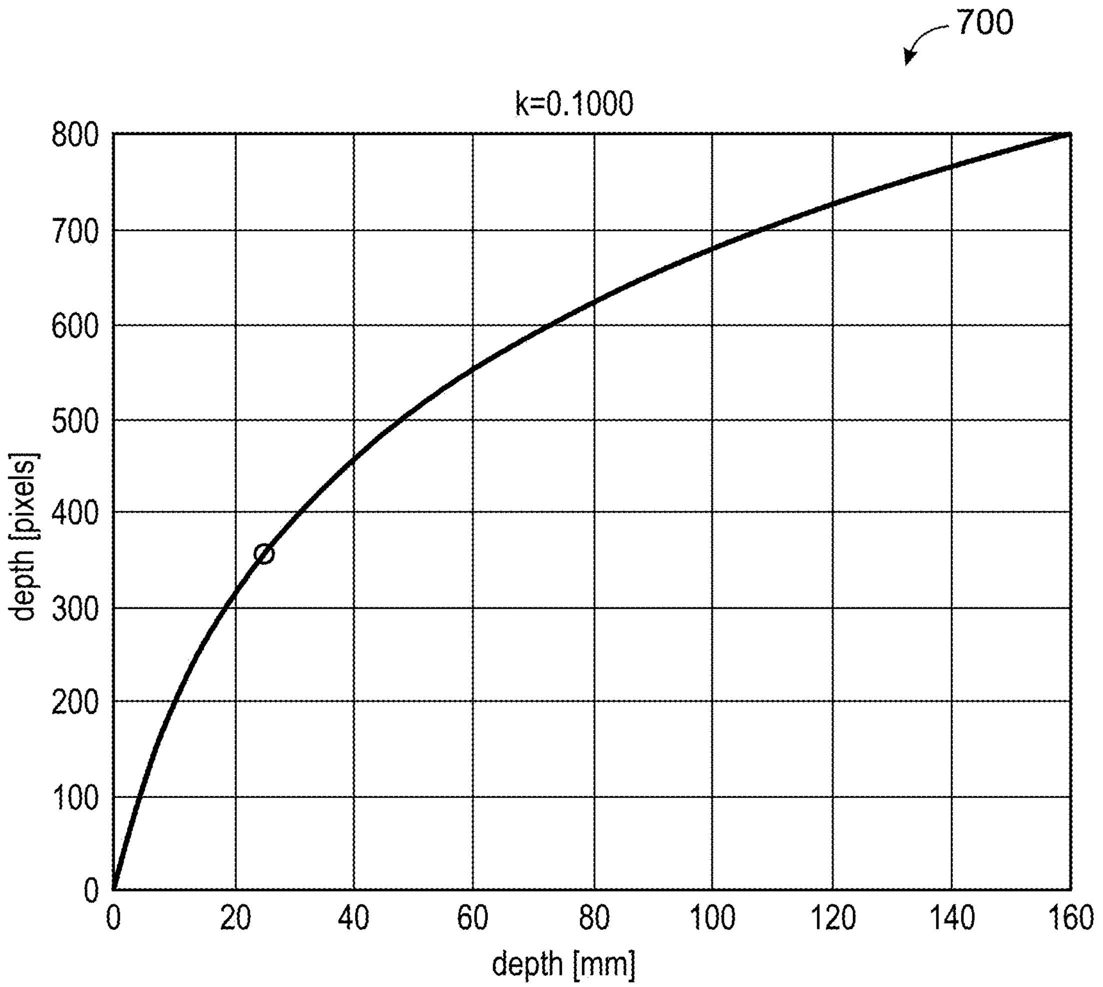

FIGS. 7A-7C are diagrams 700 of scaling techniques for generating an ultrasound image having a non-linear axial scale. As shown in FIGS. 7A-7C, the ultrasound system 100 may apply various compression values (e.g., k-values) with a u-law scaling technique to generate the ultrasound image having a non-linear axial scale. As shown in FIG. 7A, the ultrasound system 100 may use a k-value of 0.0001 which generates an ultrasound image having a substantially linear axial scale. For instance, as shown, a first range of depths from 0-20 millimeters (mm) in the subject may include 100 pixels in the ultrasound image, a second range of depths from 20-40 mm may include 100 pixels in the ultrasound image, a third range of depths of 40-60 mm in the subject may include 100 pixels in the ultrasound image, etc. As shown in FIG. 7B, the ultrasound system 100 may use a k-value of 0.0200 which generates an ultrasound image having a non-linear axial scale. For instance, as shown, a first range of depths from 0-20 mm in the subject may include 200 pixels in the ultrasound image, a second range of depths from 20-40 mm may include 120 pixels in the ultrasound image, a third range of depths of 40-60 mm in the subject may include 110 pixels in the ultrasound image, etc. As shown in FIG. 7C, the ultrasound system 100 may use a k-value of 0.1000 which generates an ultrasound image having a non-linear axial scale. For instance, as shown, a first range of depths from 0-20 mm in the subject may include 310 pixels in the ultrasound image, a second range of depths from 20-40 mm may include 140 pixels in the ultrasound image, a third range of depths of 40-60 mm in the subject may include 100 pixels in the ultrasound image, etc.

Figure 8:
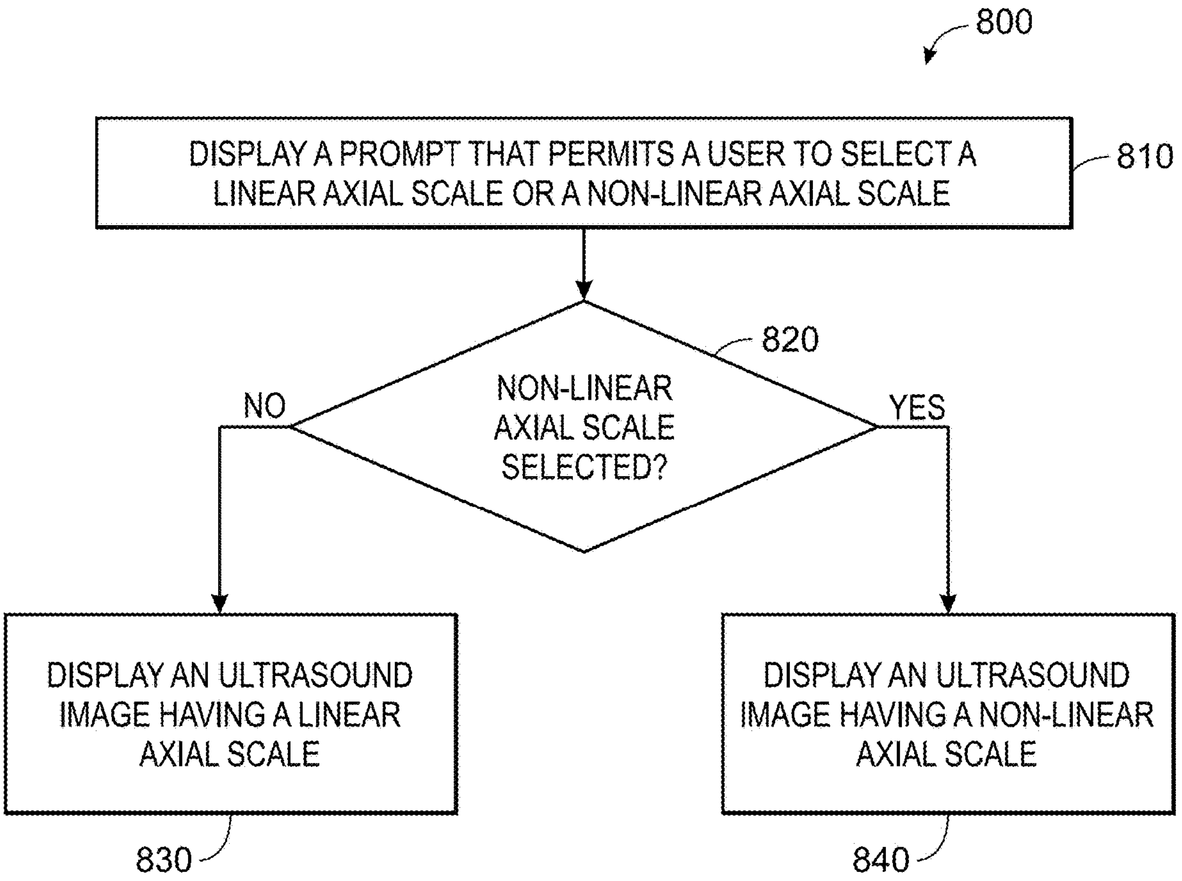
FIG. 8 is a flowchart of an example process for displaying an ultrasound image having a linear axial scale or a non-linear axial scale based on a user selection.

FIG. 8 is a flowchart of an example process 800 for displaying an ultrasound image having a linear axial scale or a non-linear axial scale based on a user selection. As shown in FIG. 8, the process 800 may include displaying a prompt that permits a user to select a linear axial scale or a non-linear axis scale (operation 810). For example, the ultrasound system 100 may display a prompt that permits a user to select a linear axial scale for displaying an ultrasound image, or select a non-linear axial scale for displaying an ultrasound image. The ultrasound system 100 may display the prompt based on acquiring ultrasound data of a region of interest of a subject, based on displaying an ultrasound image, or the like. As further shown in FIG. 8, the process 800 may include determining whether the user has selected the non-linear axial scale (operation 820). For example, the ultrasound system 100 may determine a user selection, and determine whether the user selection corresponds to the linear axial scale or the non-linear axial scale. If the ultrasound system 100 determines that the user has selected the linear axial scale (operation 820—NO), then, as further shown in FIG. 8, the process 800 may include displaying an ultrasound image having a linear axial scale (operation 830). For example, the ultrasound system 100 may display an ultrasound image having a linear axial scale. Alternatively, if the ultrasound system 100 determines that the user has selected the non-linear axial scale (operation 820—YES), then, as further shown in FIG. 8, the process 800 may include displaying an ultrasound image having a non-linear axial scale (operation 840). For example, the ultrasound system 100 may display an ultrasound image having a non-linear axial scale. In some cases, the ultrasound system 100 may switch between displaying an ultrasound image having a linear axial scale and an ultrasound image having a non-linear axial scale, and vice versa. That is, the ultrasound system 100 may dynamically switch between displaying a particular ultrasound image in either a liner axial scale or a non-linear axial scale based on a user selection.

Figure 9:
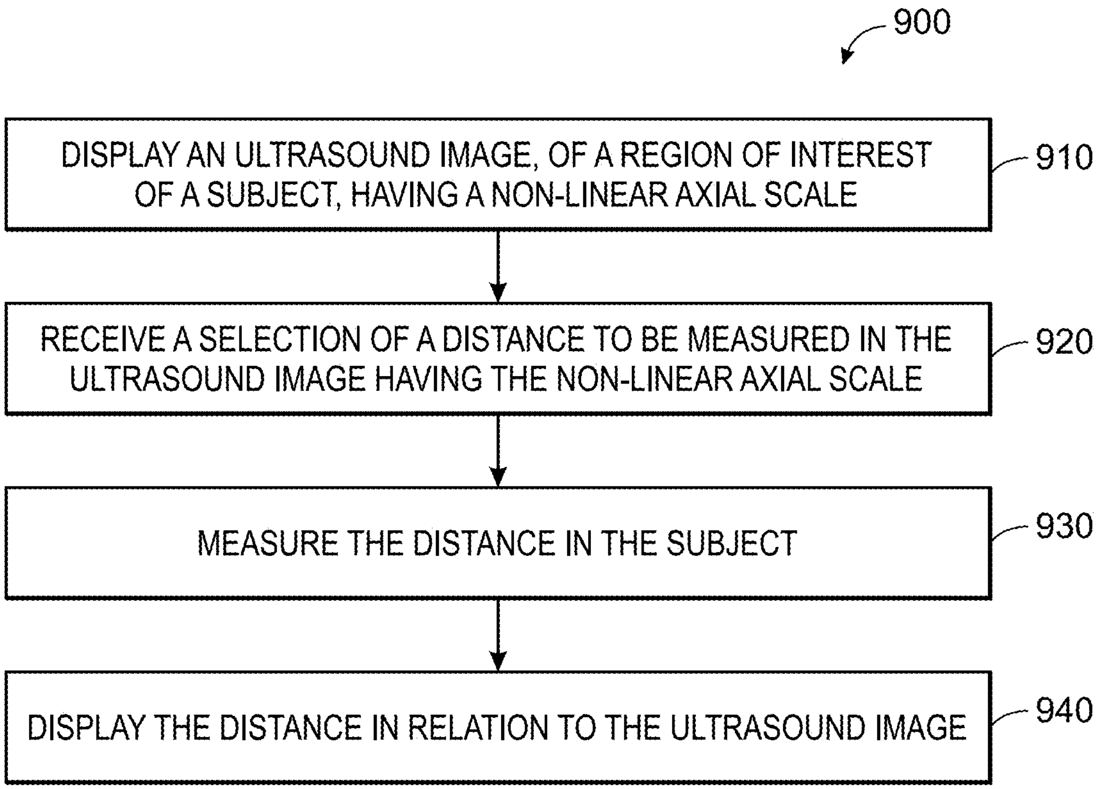
FIG. 9 is a flowchart of an example process for displaying a distance in relation to an ultrasound image based on a user selection.

FIG. 9 is a flowchart of an example process 900 for displaying a distance in relation to an ultrasound image based on a user selection. As shown in FIG. 9, the process 900 may include displaying an ultrasound image, of a region of interest of a subject, having a non-linear axial scale (operation 910). For example, the ultrasound system 100 may display an ultrasound image, of a region of interest of a subject, having a non-linear axial scale. As further shown in FIG. 9, the process 900 may include receiving a selection of a distance to be measured in the ultrasound image having the non-linear axial scale (operation 920). For example, the ultrasound system 100 may receive a selection of a distance to be measured in the ultrasound image. The ultrasound system 100 may receive the selection based on a user interaction with a user interface element of the ultrasound system 100. For instance, the user interface element may be a line, a circle, or the like, that is to be used to measure a distance in the ultrasound image. The user may interact with the user interface element to position and/or orient the user interface element with respect to a particular anatomical feature or content of the ultrasound image. As further shown in FIG. 9, the process 900 may include measuring the distance in the subject (operation 930). For example, the ultrasound system 100 may measure the distance in the subject based on the distance to be measured in the ultrasound image. The ultrasound system 100 may measure the distance in the subject based on a scale that is an indication of a relationship between distances on the ultrasound image and the corresponding actual distances in the subject. As further shown in FIG. 9, the process 900 may include displaying the distance in relation to the ultrasound image (operation 940). For example, the ultrasound system 100 may display the distance in relation to the ultrasound image. The ultrasound system 100 may display the distance in relation to the ultrasound image by displaying a numerical value for the distance that is overlaid on the ultrasound image adjacent to the user interface element. Alternatively, the ultrasound system 100 may display the distance in relation to the ultrasound image by displaying a numerical value for the distance in a predetermined positon on the display 116 of the ultrasound system 100.

Figure 10:
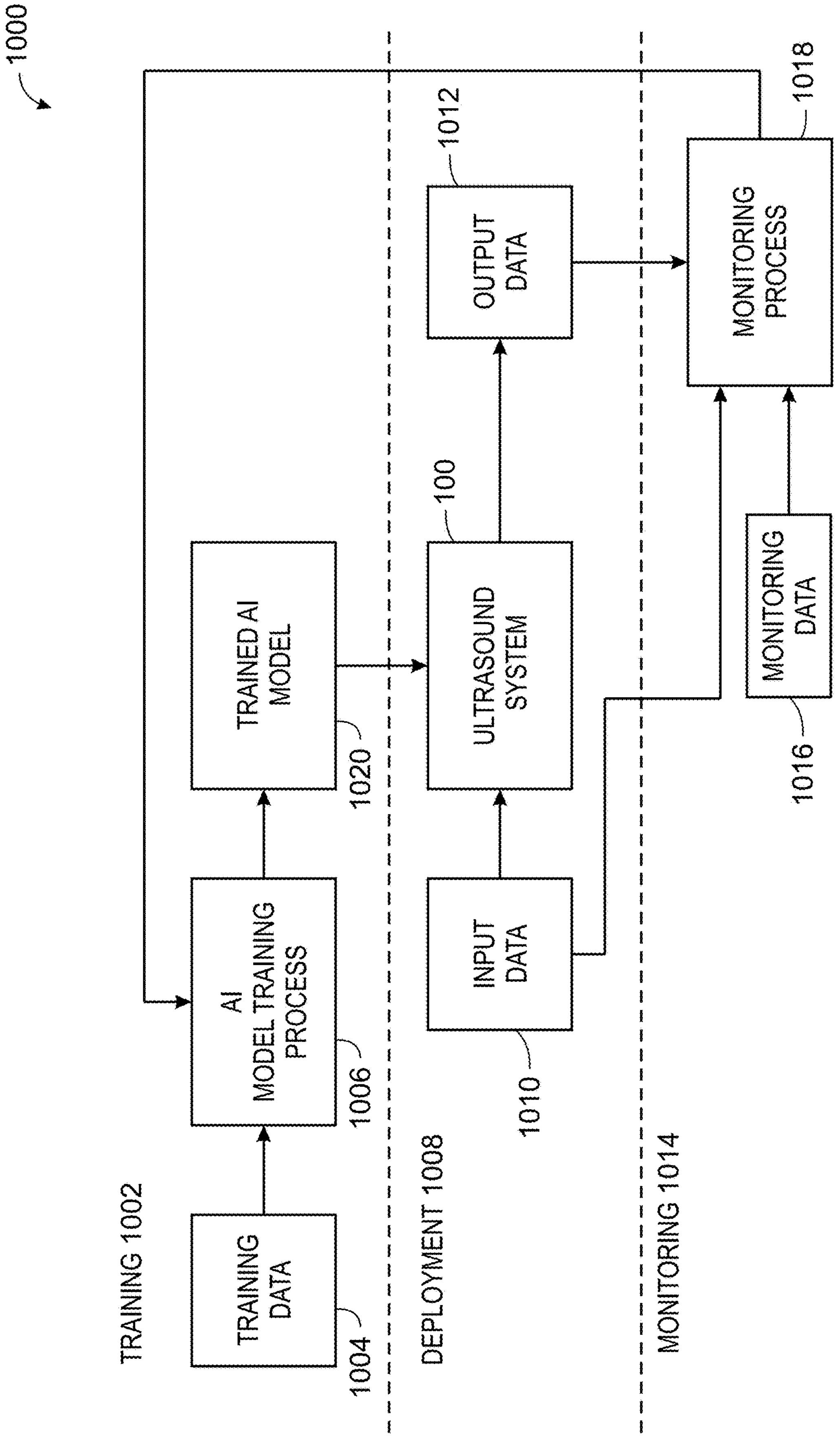
FIG. 10 is a diagram of an example process for training, deploying, and monitoring an artificial intelligence (AI) model.

FIG. 10 is a diagram 1000 of an example process for training, deploying, and monitoring an AI model 1020. According to an embodiment, the ultrasound system 100 may use one or more AI models 1020. The one or more AI models 1020 may be associated with a training phase 1002, a deployment phase 1008, and a monitoring phase 1014. In the training phase 1002, the ultrasound system 100 (or an external system) may receive and process training data 1004 to generate a trained model 1020. The training data 1004 may be generated, received, or otherwise obtained from internal and/or external resources.

Generally, the trained model 1020 may include a set of variables (e.g., nodes, neurons, filters, or the like) that are tuned (e.g., weighted, biased, or the like) to different values via the application of the training data 1004. According to an embodiment, the training process may employ supervised, unsupervised, semi-supervised, and/or reinforcement learning processes to train the model 1020. According to an embodiment, a portion of the training data 1004 may be withheld during training and/or used to validate the trained model 1020.

For supervised learning processes, the training data 1004 may include labels or scores that may facilitate the training process by providing a ground truth. For example, the labels or scores may indicate an output of the AI model 1020. Training may proceed by feeding the training data 1004 into the AI model 1020. The AI model 1020 may have variables set at initialized values (e.g., at random, based on Gaussian noise, based on pre-trained values, or the like). The AI model 1020 may generate an output based on the training data 1004 being input to the AI model 1020. The output may be compared with the corresponding label or score (e.g., the ground truth) indicating the known output, which may then be back-propagated through the AI model 1020 to adjust the values of the variables. This process may be repeated for a plurality of samples at least until a determined loss or error is below a predefined threshold. According to an embodiment, some of the training data 1004 may be withheld and used to further validate or test the trained AI model 1020.

For unsupervised learning processes, the training data 1004 may not include pre-assigned labels or scores to aid the training process. Instead, unsupervised learning processes may include clustering, classification, or the like, to identify naturally occurring patterns in the training data 1004. As an example, the training data 1004 may be clustered into groups based on identified similarities and/or patterns. K-means clustering or K-Nearest Neighbors may also be used, which may be supervised or unsupervised. Combinations of K-Nearest Neighbors and an unsupervised cluster technique may also be used. For semi-supervised learning, a combination of training data 1004 with pre-assigned labels or scores and training data without pre-assigned labels or scores may be used to train the AI model 1020.

When reinforcement learning is employed, an agent (e.g., an algorithm) may be trained to make a decision from the training data 1004 through trial and error. For example, based on making a decision, the agent may then receive feedback (e.g., a positive reward if the prediction was above a predetermined threshold), adjust its next decision to maximize the reward, and repeat until a loss function is optimized.

After being trained, the trained model 1020 may be stored and subsequently applied by the ultrasound system 100 during the deployment phase 1008. For example, during the deployment phase 1008, the trained AI model 1020 executed by the ultrasound system 100 may receive input data. During the deployment phase 1008, the trained AI model 1020 may perform one or more operations as described in connection with FIGS. 3, 6, 8, and/or 9.

After being deployed, the trained AI model 1020 may be monitored during the monitoring phase 1014. For example, during the monitoring phase 1014, the AI model 1020 may generate monitoring data that is used to monitor the trained AI model 1020. The monitoring data may include data that identifies an output as determined by an operator. During the monitoring phase 1014, monitoring data may be analyzed along with the predicted output data and input data to determine an accuracy of the trained AI model 1020. According to an embodiment, based on the analysis, the process may return to the training phase 1002, where values of one or more variables of the AI model 1020 may be adjusted to improve the accuracy of the AI model 1020.

Although the embodiments herein are described in connection with ultrasound systems and ultrasound images, it should be appreciated that the embodiments herein are applicable to other types of medical imaging modalities and other types of medical images (e.g., CT images, MRI images, etc.). Further, although some embodiments herein are described in connection with lung ultrasound, it should be understood that the embodiments herein are applicable to any other region of interest of a subject (e.g., the heart, the liver, etc.). Further still, although some embodiments herein describe a non-linear axial scale, it should be understood that the embodiments herein are applicable to non-linear horizontal scales.

In this way, some embodiments herein provide an improvement to the technical field of ultrasound imaging by providing for the generation of a new type of ultrasound image that is a single continuous image that has a non-linear axial scale. Further, some embodiments herein provide an improvement to ultrasound systems by permitting the ultrasound system to generate a single continuous image that has a non-linear axial scale. The non-linear axial scale may permit the simultaneous viewing of the near-field and the far-field in a manner that provides for increased detail and resolution in the near-field. Accordingly, a clinician may observe the near-field details while appreciating the full imaging depth in a single continuous ultrasound image.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:

1. An ultrasound system comprising:

a memory configured to store instructions; and one or more processors configured to execute the instructions to:

acquire raw ultrasound data of a region of interest of a subject;

generate an ultrasound image of the region of interest of the subject having a non-linear axial scale by transforming the raw ultrasound data that has not been scan-converted; and display the ultrasound image having the non-linear axial scale based on generating the ultrasound image.

2. The ultrasound system of claim 1, wherein a first region of the ultrasound image includes a linear axial scale, and wherein a second region of the ultrasound image includes the non-linear axial scale.

3. The ultrasound system of claim 1, wherein the one or more processors are further configured to:

transform the raw ultrasound data by applying u-law scaling.

4. The ultrasound system of claim 1, wherein the one or more processors are further configured to:

determine a depth at which to transition a scale of the ultrasound image.

5. The ultrasound system of claim 1, wherein a first region of the ultrasound image includes a first linear axial scale, and wherein a second region of the ultrasound image includes a second linear axial scale that is different than the first linear axial scale.

6. The ultrasound system of claim 1, wherein the ultrasound image includes a first region corresponding to a first range of depths in the subject, wherein the ultrasound image includes a second region corresponding to a second range of depths in the subject, wherein the first range of depths is the same as the second range of depths, and wherein the first region includes a first number of pixels that is greater than a second number of pixels in the second region.

7. The ultrasound system of claim 1, wherein the ultrasound image is a single continuous ultrasound image.

8. The ultrasound system of claim 1, wherein the one or more processors are further configured to:

determine a depth of pleura in the region of interest of the subject using an image processing technique or an artificial intelligence (AI) model, wherein the one or more processors are configured to generate the ultrasound image having the non-linear axial scale based on determining the depth of the pleura, and wherein a first region of the ultrasound image above the depth of the pleura includes a first axial scale, and wherein a second region of the ultrasound image below the depth of the pleura includes a second axial scale that is different than the first axial scale.

9. The ultrasound system of claim 1, wherein the one or more processors are further configured to:

display a prompt that permits a user to select a linear axial scale or the non-linear axial scale; and receive a user selection that selects the non-linear axial scale, wherein the one or more processors are configured to display the ultrasound image having the non-linear axial scale based on receiving the user selection.

10. The ultrasound system of claim 1, wherein the ultrasound image is a three-dimensional (3D) ultrasound image having the non-linear axial scale.

11. A method comprising:

acquiring raw ultrasound data of a region of interest of a subject;

generating an ultrasound image of the region of interest of the subject having a non-linear axial scale by transforming the raw ultrasound data that has not been scan-converted; and displaying the ultrasound image having the non-linear axial scale based on generating the ultrasound image.

12. The method of claim 11, wherein a first region of the ultrasound image includes a linear axial scale, and wherein a second region of the ultrasound image includes the non-linear axial scale.

13. The method of claim 11, further comprising:
transforming the raw ultrasound data by applying μ-law scaling.

14. The method of claim 11, further comprising:
determining a depth at which to transition a scale of the ultrasound image.

15. The method of claim 11, wherein a first region of the ultrasound image includes a first linear axial scale, and wherein a second region of the ultrasound image includes a second linear axial scale that is different than the first linear axial scale.

16. The method of claim 11, wherein the ultrasound image includes a first region corresponding to a first range of depths in the subject, wherein the ultrasound image includes a second region corresponding to a second range of depths in the subject, wherein the first range of depths is the same as the second range of depths, and wherein the first region includes a first number of pixels that is greater than a second number of pixels in the second region.

17. The method of claim 11, wherein the ultrasound image is a single continuous ultrasound image.

18. The method of claim 11, further comprising:
determining a depth of pleura in the region of interest of the subject using an image processing technique or an artificial intelligence (AI) model,
wherein the generating the ultrasound image comprises generating the ultrasound image having the non-linear axial scale based on determining the depth of the pleura, and
wherein a first region of the ultrasound image above the depth of the pleura includes a first axial scale, and wherein a second region of the ultrasound image below the depth of the pleura includes a second axial scale that is different than the first axial scale.

19. The method of claim 11, further comprising:
displaying a prompt that permits a user to select a linear axial scale or the non-linear axial scale; and
receiving a user selection that selects the non-linear axial scale,
wherein the displaying the ultrasound image comprises displaying the ultrasound image having the non-linear axial scale based on receiving the user selection.

20. A non-transitory computer-readable medium storing instructions that, when executed by one or more processors, cause the one or more processors to:
acquire raw ultrasound data of a region of interest of a subject;
generate an ultrasound image of the region of interest of the subject having a non-linear axial scale by transforming the raw ultrasound data that has not been scan-converted; and
display the ultrasound image having the non-linear axial scale based on generating the ultrasound image.

* * * * *